United States Patent [19]

Ni et al.

[11] Patent Number: 5,658,758

[45] Date of Patent: Aug. 19, 1997

[54] POLYNUCLEOTIDES ENCODING CYTOSTATIN I

[76] Inventors: Jian Ni, 305 West Side Dr., Apt. 204, Gaithersburg, Md. 20878; Reiner Gentz, 13404 Fairland Park Dr., Silver Spring, Md. 20904; Guo-Liang Yu, 13524 Straw Bale La., Darnestown, Md. 20878; Craig A. Rosen, 22400 Rolling Hill Rd., Laytonsville, Md. 20882

[21] Appl. No.: 409,731

[22] Filed: Mar. 24, 1995

[51] Int. Cl.$^6$ ............................ C12N 15/12; C07K 14/475

[52] U.S. Cl. .................. 435/69.1; 435/70.1; 435/252.23; 435/320.1; 435/172.3; 435/325; 435/348; 435/419; 435/358; 435/365; 935/11; 935/22; 935/66; 935/70; 536/23.1; 536/23.5

[58] Field of Search ................................ 536/23.1, 23.5; 435/69.1, 70.1, 172.3, 260.2, 320.1, 252.3; 935/11, 22, 27, 31, 52, 55, 58, 66, 70; 530/350

[56] References Cited

PUBLICATIONS

Grosse, Richard, et al., "Antibodies Against Mammary Derived Growth Inhibitor (MDGI) React With A Fibroblast Growth Inhibitor and With Heart Fatty Acid Binding Protein," Biochemical and Biophysical Research Communications vo. 148, No. 3, Nov. 1987, p. 1425.

Grosse, Richard, et al., "Purification, Biological, Assay, and Immunoassay of Mammary–Derived Growth Inhibitor," Methods in Enzymology, vol. 198, 1991, pp. 425–440.

Brandt, Ralf and Grosse, Richard, "Purification of a Mammary–Derived Growth Inhibitor (MDGI) Related Polypeptide Expressed During Pregnancy," Biochemical and Biophysical Research Communications, vol. 189, No. 1, 1992, pp. 406–413.

Bansal, M.P. and Medina, D., "Expression of Fatty Acid–binding Proteins in the Developing Mouse Mammary Gland," Biochemical and Biophysical Research Communications, vol. 191, 1993, pp. 61–69 (Abstract).

Lehmann, W., Widmaier, R. and Langen, P., "Response of Different Mammary Epithelial Cell Lines to a Mammary Derived Growth Inhibitor (MDGI)," Biomed Biochim Acta vol. 48, 1989, pp. 143–151 (Abstract).

Behlke, J., Mieth, M., Bohmer, F.D., Grosse, R., "Hydrodynamic and Circular Dichroic Analysis of Mammary–derived Growth Inhibitor (MDGI)," Biochemical and Biophysical Research Communications, vol. 161, 1989, pp. 363–370 (Abstract).

Brandt, R., Pepperle, M., Otto, A., Kraft, R., Boehmer, F.D., Grosse, R., "A 13–Kilodalton Protein Purified From Milk Fat Globule Membranes is Closely Related to a Mammary–Derived Growth Inhibitor," Biochemistry, vol. 27, 1988, pp. 1420–1425 (Abstract).

Bohmer, F.D., Lehmann, W., Schmidt, H.E., Langen, P., Grosse, R., "Purification of a Growth Inhibitor for Ehrlich Ascites Mammary Carcinoma Cells from Bovine Mammary Gland," Experimental Cell Research, vol. 150, 1984, pp. 466–476 (Abstract).

Spener, Friedrich, Unterberg, Christian, Borchers, Torsten, and Grosse, Richard, "Characteristics of Fatty Acid–Binding Proteins and Their Relation to Mammary–Derived Growth Inhibitor," Molecular and Cellular Biochemistry, vol. 98, 1990, pp. 57–68.

Yang, Yanmin, Spitzer, Eva, et al., "Members of the Fatty–Acid Binding Protein Family Are Differentiation Factors for the Mammary Gland," The Journal of Cell Biology, vol., 127, No. 4 1994, pp. 1097–1109.

Grosse, Richard, Bohmer, Frank D., et al., "Mammary–Derived Growth Inhibitor (MDGI)," Genes, Oncogenes, and Hormones: Advances in Cellular and Molecular Biology of Breast Cancer, (R.B. Dickson and M.E. Lippman (eds.)) 1991.

Wobus, A.M., Zschiesche, W., and Grosse, R., "Differentiation–Promoting Effects of Mammary–Derived Growth Inhibitor (MDGI)," Medline, 1990 (Abstract).

Treuner, M., Kozak, C.A., Gallahan, D., Grosse, R., and Muller, T., "Cloning and Characterization of the Mouse Gene Encoding Mammary–Derived Growth Inhibitor Heart/Fatty Acid–binding Protein," Medline, 1994 (Abstract).

Zavizion, B., Politis, I., Gorewit, R.C., Turner, J.D., Spitzer, E., Grosse, R., "Effect of Mammary–Derived Growth Inhibitor on Proliferation of MAC–T Bovine Mammary Epithelial Cells," Medline, 1994 (Abstract).

Erdmann, B., Breter, H., "Irregular Distribution of Mammary–Derived Growth Inhibitor in the Bovine Mammary Epithelium," Medline, 1994 (Abstract).

Grosse, R., Bohmer, F.D., Binas, B., Kurtz, A., et al., "Mammary–Derived Growth Inhibitor (MDGI)," Medline, 1994 (Abstract).

Vogel, F., Mueller, T., and Grosse, R., "Is the Mammary–Derived Growth Inhibitor Related 70 kD Antigen, Identified in Nuclei, A Nuclear Receptor for MDGI or its Hydrophobic Ligands?" Medline, 1994 (Abstract).

Binas, B., Spitzer, E., Zschiesche, W., et al., "Hormonal Induction of Functional Differentiation and Mammary–Derived Growth Inhibitor Expression in Cultured Mouse Mammary Gland Explants," Medline, 1994 (Abstract).

Politis, I., Gorewit, R.C., Muller, T., Grosse, R., "Mammary–Derived Growth Inhibitor Protein and Messenger Ribonucleic Acid Concentrations in Different Physiological States of the Gland," Medline, 1994 (Abstract).

Politis, I., Gorewit, R.C., Muller, T., Grosse, R., "Mammary–Derived Growth Inhibitor in Lactation and Involution," Medline, 1994 (Abstract).

(List continued on next page.)

*Primary Examiner*—John Ulm
*Assistant Examiner*—Prema Mertz

[57] ABSTRACT

A human cytostatin I polypeptide and DNA encoding such polypeptide and a procedure for producing such polypeptide by recombinant techniques is disclosed. Also disclosed are methods for utilizing such polypeptide for the treatment of cancers, particularly breast cancer, leukemias, and other matastases.

12 Claims, 10 Drawing Sheets

OTHER PUBLICATIONS

Grosse, R., Boehmer, F.D., Langen, P., Kurtz, A., et al., "Purification, Biological Assay, and Immunoassay of Mammary–Derived Growth Inhibitor," Medline, 1994 (Abstract).

Wallukat, G., Boehmer, F.D., Engstroem, U., Langen, P., et al., "Modulation of the Beta–Adrenergic–Response in Cultured Rat Heart Cells II. Mammary–Derived Growth Inhibitor Blocks Induction of Beta–Adrenergic Supersensitivity . . . " Medline, 1994 (Abstract).

Erdmann, B., Binas, B., "Application of the Immunogold–Silver Staining Method to Localize a Mammary–Derived Growth Inhibitor," Medline, 1994 (Abstract).

Yang, Y., Spitzer, E., Kenney, N., Zschiesche, W., et al., "Members of the Fatty Acid Binding Protein Family are Differentiation Factors for the Mammary Gland," Medline, 1994 (Abstract).

Breter, H., and Erdmann, B., "Localiztion of Mammary–Derived Growth Inhibitor in Capillary Endothelial Cells of the Bovine Mammary Gland," Medline, 1994 (Abstract).

Bohmer, F.D., Kraft, R., Otto, A., Wernstedt, D., et al., "Identification of a Polypeptide Growth Inhibitor from Bovine Mammary Gland, etc." Journal of Biological Chemistry, vol. 262, 1987, pp. 15137–15143.

Lowe, J.B., Strauss, A.W., Gordon, J.I., "Expression of a Mammalian Fatty Acid–Binding Protein in *Escherichia coli*," Journal of Biological Chemistry, Vol. 259, 1984, pp. 12696–12704.

Bohmer, F.D., Lehmann, W., Noll, F., et al., "Specific Neutralizing Antiserum Against a Polypeptide Growth Inhibitor for Mammary Cells Purified From Bovine Mammary Gland," Biochim Biophys Acta, vol. 846, 1985, pp. 145–154 (Abstract).

Newcomer, Marcia E., "Retinoid–Binding Proteins: Structural Determinants Important For Function," The FASEB Journal, No. 9, 1995, pp. 229–239.

Krieg, Peter, Feil, Sabine, Furstenberger, Gerhard, et al., "Tumor–Specific Overexpression of a Novel Keratinocyte Lipid–Binding Protein," Journal of Biological Chemistry, vol. 268, No. 23, 1993, pp. 17362–17369.

Yeung A. (1994) vol. 55/12–B of Dissertation Abstracts International p. 5300.

Yeung et al. (1994) FASEB Journal, vol. 8 (4–5) A117.

Tong et al. (1990) FASEB, Part I, J4(3) A487.

Amemiya et al. "Cytostatin, A Novel Inhibitor Of Cell Adhesion To Components Of Extracellular Matrix Produced by *Streptomuces sp.* MJ654–NF4I", *Jnl. of Antibiotics*, 47(5):536–540 (May, 1994).

Amemiya et al. "Cytostatin, A Novel Inhibitor Of Cell Adhesion To Components Of Extracellular Matrix Produced By *Streptomuces sp.* MJ654–NF4 II", *Jnl. of Antibiotics*, 47(5):541–544 (May, 1994).

Yamazaki et al. "Screening for Apoptosis Inducers in Microbial Products and Induction of Apoptosis by Cytostatin", *Jnl. of Antibiotics*, 48(10):1138–1140 (Oct. 1995).

NUCLEOTIDE AND AMINO ACID SEQUENCE OF HUMAN CYTOSTATIN I

```
          10                  30                  50
CACGAGCTGGAATCTCTCAGCCTCACCTGCCAGACAACACCCCCTCCTTCCTCACCCTGT
          70                  90                 110
TTCCTGCATTCTCCTGAAACCTTCATCCACACAATGCCTCCCAACCTCACTGGCTACTAC
                                      M  P  P  N  L  T  G  Y  Y
         130                 150                 170
CGCTTTGTTTCGCAGAAGAACATGGAGGACTACCTGCAAGCCCTAAACATCAGCTTGGCT
 R  F  V  S  Q  K  N  M  E  D  Y  L  Q  A  L  N  I  S  L  A
         190                 210                 230
GTGCGGAAGATCGCGCTGCTGCTGAAGCCGGACAAGGAGATCGAACACCAGGGCAACCAC
 V  R  K  I  A  L  L  L  K  P  D  K  E  I  E  H  Q  G  N  H
         250                 270                 290
ATGACGGTGAGGACGCTCAGCACCTTCCGAAACTACACTTTGCAGTTTGATGTGGGAGTG
 M  T  V  R  T  L  S  T  F  R  N  Y  T  L  Q  F  D  V  G  V
         310                 330                 350
CAGAAAGGGGAGGTCCCCAACCGGGGCTGGAGACACTGGCTGGAGGGAGAGTTGCTGTAT
 Q  K  G  E  V  P  N  R  G  W  R  H  W  L  E  G  E  L  L  Y
         370                 390                 410
CTGGAACTGACTGCAAGGGATGCAGTGTGCGAGCAGGTCTTCAGGAAGGTCAGATAGCCG
 L  E  L  T  A  R  D  A  V  C  E  Q  V  F  R  K  V  R
         430                 450                 470
GAGAGGAGCCAAGATCCCTCCAGACAGCACCAGCTCACAGACGCTCTTGTTGTGCCCCCT
         490                 510                 530
TCAAGCCCAGATTGTGCCAGGTCAGCTGTCCCTTCCTCTGGCCACCTTTCCTCCCTCTGG
         550                 570                 590
GTCCCTCCTCACCCCTCCCCGTGTTAATCTGTAACTTGGAGCCCCCAGGACAAAGTCCTT
         610                 630                 650
TCTCACACTCCACTGCCCAATAGTGACCTCACTTCCAGGTCAAGGTCTGGCGTCCCAAAT
         670                 690                 710
GAAAGAAGCAGGCAAAGGGAAGGAGCCCCTGAGGACAACCAATCTCCGCTCTCTCCTGTC
         730                 750                 770
CATTTGACCTCTTCTTTTCCTTCTAAGAAAGAACTAAGCTTTGGGCATTTGGCGATTAGT
         790                 810                 830
GAAAATTCTATCCTGATGGACTTCTGGAAAACTGTGACTGGGGTTCAACAGTTTAAACAG
         850
GGGCTACTGGGGGAAAAAAAA
```

FIG.1

```
          M . . . G . . . . . N . . . Y . . . . L . . . . . . A . . .    Consensus #1
          M P D A F L G T W K L V S S E N F D D Y M K A L G V G F A T    Majority
                            10                  20                  30

1  M P N L T G Y Y R F V S Q K N M E D Y L Q A L N I S L A V             HTOBH93
 1  M A D A F V G T W K L V D S K N F D D Y M K S L G V G F A T           MDGI
 1  M P V D F T G Y W K M L V N E N F E E Y L R A L D V N V A L           CRBPI
 1  M T R D Q N G T W E M E S N E N F E G Y M K A L D I D F A T           CRBPII
 1  M V D A F L G T W K L V D S K N F D D Y M K S L G V G F A T           FABP
 1  M S N K F L G T W K L V S S E N F D D Y M K A L G V G L A T           Myelin P2

. . . . . . . . . . . . . . . I . G . . . . . . . T . S T F . N   Consensus #1
          R K I A S L L K P T K I I E K D G D I I K T L S T F K N         Majority
                            40                  50                  60

31  R K I A L L L K P D K E I E H Q G N H M T V R T L S T F R N           HTOBH93
31  R Q V A S M T K P T T I I E K N G D T I T I K T Q S T F K N           MDGI
31  R K I A N L L K P D K E I V Q D G D H M I R T L S T F R N             CRBPI
31  P K I A V R L T Q T K V I D Q D G D N F K T K T T S T F R N           CRBPII
31  R Q V A S M T K P T T I I E K N G D I L T L K T H S T F K N           FABP
31  R K L G N L A K P T V I I S K K G D I I T I R T E S T F K N           Myelin P2
```

| | | | | | | Consensus #1 Majority |
|---|---|---|---|---|---|---|
| . I L E L T H G G V V C T Q V F E K . . . A . | | | | | | |
| | . | . | V | . | . K . . . | |
| | | | | | | |

```
               .  I L E L T H G G V V C T Q V F E K . . . A -
                                                           140
                           130
 89  Y L E L T A R D A V C E Q V F R K V - R
115  I L T L T H G S V V S T R T Y E K - E A
117  H L E M R V E G V V C K Q V F K K V - Q
117  Y L E L T C G D D Q V C R Q V F K K I - K
115  I L T L T H G T A V C T R T Y E K - E A
115  V A E C K M K G V V C T R I Y E K I - V
```

Consensus #1
                                                Majority

HTOBH93
                                                MDGI
                                                CRBPI
                                                CRBPII
                                                FABP
                                                Myelin P2

FIG.2C

POLYNUCLEOTIDES ENCODING CYTOSTATIN I

This invention relates to newly identified polynucleotides, polypeptides encoded by such polynucleotides, the use of such polynucleotides and polypeptides, as well as the production of such polynucleotides and polypeptides. More particularly, the polypeptide of the present invention is cytostatin I, a polypeptide modulating cellular metabolism. The invention also relates to inhibiting the action of such polypeptides.

BACKGROUND

The cytostatin I of the present invention has been putatively identified as a growth inhibitory protein. This identification has been made as a result of amino acid sequence homology to mammary-derived growth inhibitor(MDGI) and direct measurements on cell growth.

Mammary-derived growth inhibitor (MDGI) is a cell growth inhibitor and differentiation factor firstly purified mammary carcinoma cells Ehrlich ascites, and then from cows milk and bovine mammary gland (Grosse et al. 2 references). MDGI inhibits proliferation of mammary epithelial cell lines in a dose-dependent and reversible manner. Maximal inhibition of cell proliferation by purified MDGI is in the range of 35 to 50%. In these cells half-maximal inhibition was obtained with about $10^{-10}$M MDGI (1 ng/ml). Inhibition was abolished by simultaneously adding epidermal growth factor (EGF), insulin. MDGI also inhibits the proliferation of several other permanent mammary carcinoma cell lines. MDGI has been shown to be immunologically related to a fibroblast growth inhibitor.

Peptides that locally signal growth cessation and stimulate differentiation of the developing epithelium are very important for mammary gland development. Recombinant and wild-type forms of mammary-derived growth inhibitor (MDGI) and heart-fatty acid binding protein (FABP), which belong to the FABP family, specifically inhibit growth of normal mouse mammary epithelial cells (MEC) and promote morphological differentiation, stimulates its own expression and promotes milk protein synthesis. Selective inhibition of endogenous MDGI expression in MEC by antisense phosphorothioate oligonucleotides suppresses appearance of alveolar end buds and lowers the beta- casein level in organ cultures. Furthermore, MDGI suppresses the mitogenic effects of EGF, and EGF antagonizes the activities of MDGI. Finally, the regulatory properties of MDGI can be fully mimicked by an 11-amino acid sequence, represented in the COOH terminus of MDGI and a subfamily of structurally related FABPs. MDGI is the first known growth inhibitor which promotes mammary gland differentiation. The amount of MDGI increased dramatically with the onset of lactation after delivery. Recent studies shows that a new posttranslational processing form of MDGI, MDGI 2, not present in lactation, was found in the bovine gland during pregnancy.(Brandt et al, Biochem Biophy Res Comm Vol 189, p406, Nov. 30, 1992) To date, bovine, rat and mouse MDGI have been identified but no human MDGI or MDGI-like protein.

There is no sequence homology between MDGI and other known growth inhibitors. Thus, along with interferons, transforming growth factors β, and tumor necrosis factors, MDGI is one of the few naturally occurring growth inhibitors for mammary epithelium identified so far. Sequence analysis revealed extensive sequence homology of MDGI to a family of low molecular mass hydrophobic ligand-binding proteins, among them a fatty acid-binding protein (FABP) from brain and heart, myelin P2, a differentiation associated protein in adipocytes (p422), gastrotropin, and the cellular retinoic acid-binding protein (CRABP). These proteins basically share two properties in common: they bind hydrophobic ligands such as long-chain fatty acids, retinoids, and eicosanoids, and they are expressed in a differentiation-dependent manner in mammary gland, heart, liver, brain, or intestine. All these proteins act intracellularly except MDGI and gastrotropin, which act extracellularly in vitro. The C-terminus of MDGI residues 126–130 are identical to residues 108–112 of bovine growth hormone. This stretch of amino acids is part of a sequence of growth hormone that is essential for its biological activity. Synthetic peptides corresponding to the MDGI-sequence, residue 121–131 mimic the effects of MDGI. The functions of these MDGI proteins are not yet well-defined, although a role in fatty acid transport, sequestration, or metabolism has been widely discussed. Interaction with as yet unknown hydrophobic ligands might play a functional role in the mechanism of growth inhibition excerted by MDGI. It is proposed that MDGI may act in an autocrine manner as a growth inhibitor, however, MDGI lack a signal sequence for membrane translocation, most of MDGI has an intracellular localization. With regard to the secretion, an analogy might exit to other growth factors that also lack a signal sequence like FGF and PG-ECGF. In those cases cell damage as a possible way of secretion, or the existence of related factors with a signal sequence as a physiological ligands of the respective surface receptors, have been discussed.

Among other activities, MDGI reportedly may inhibit c-fos, c-myc and c-ras expression MDGI has differentiation-promoting activity on mouse pluripotent embryonic stem cells and supports the commitment of undifferentiated ESC for neural differentiation. It is also suggested that MDGI may be involved in the regulation of endothelial cell proliferation.

MDGI inhibits the induction of supersensitivity of neonatal rat heart muscle cells for beta-adrenergic receptors by lipoxygenase metabolites and various agents. The inhibitory activity of MDGI related to the induction of supersensitivity for hydrophilic beta-adrenergic agonists might point to a physiological role for a close relative of MDGI—the cardiac fatty acid-binding protein (H-FABP). One function of H-FABP could be to protect, the heart, under pathophysiological conditions, from lipoxygenase metabolites causing supersensitivity of beta-adrenergic receptors. Thus, H-FABP may be a physiological modulator of beta-adrenergic responses in the cardiac muscle.

In accordance with one aspect of the present invention, there is provided a novel mature polypeptide which is Cytostatin I, as well as biologically active and diagnostically or therapeutically useful fragments, analogs and derivatives thereof. The polypeptide of the present invention is of human origin.

In accordance with another aspect of the present invention, there are provided isolated nucleic acid molecules encoding human cytostatin I, including mRNAs, DNAs, cDNAs, genomic DNAs as well as analogs and biologically active and diagnostically or therapeutically useful fragments thereof.

In accordance with yet a further aspect of the present invention, there is provided a process for producing such polypeptide by recombinant techniques comprising culturing recombinant prokaryotic and/or eukaryotic host cells, containing a human cytostatin I nucleic acid sequence, under conditions promoting expression of said protein and subsequent recovery of said protein.

In accordance with yet a further aspect of the present invention, there is provided a process for utilizing such polypeptide, or polynucleotide encoding such polypeptide for therapeutic purposes, for example, as a cell growth inhibitor and as to cause differentiation stimulatory activity on various responsive types of tissues and cells.

In accordance with yet a further aspect of the present invention, there is also provided nucleic acid probes comprising nucleic acid molecules of sufficient length to specifically hybridize to human cytostatin I sequences.

In accordance with yet a further aspect of the present invention, there are provided antibodies against such cytostatin I polypeptides.

In accordance with another aspect of the present invention, there are provided cytostatin I agonists which mimic Cytostatin I and bind to the cytostatin I receptors to elicit growth inhibitory responses or which stimulate differentiation-promoting activity on progenitory cell types.

In accordance with yet another aspect of the present invention, there are provided antagonists to such polypeptides, which may be used to inhibit the action of such polypeptides, for example, in the treatment of excessive inhibition of cell or tissue growth or inappropriate differentiation stimulatory activity.

There is a need for a human MDGI-like protein and the gene encoding it. These and other aspects of the present invention should be apparent to those skilled in the art from the teachings herein.

The following drawings are illustrative of embodiments of the invention and are not meant to limit the scope of the invention as encompassed by the claims.

SUMMARY

Human cytostatin I is described for the first time together with its use as in inhibiting growth and stimulating differentiation of human cells. Translated full length cytostatin I coding sequence has good homology with mouse mammary-derived growth inhibitor (MDGI). MDGI was originally identified as the cellular retinoic acid-binding protein (CRABP). Both CRABP and MDGI belong to a family of proteins known to bind hydrophobic ligands, referred to as Fatty acid binding proteins (FABPs). Cytostatin I is 33% identical and 63% similar to mouse MDGI. Cytostatin I is highly expressed in spleen and kidney, moderately expressed in liver and thymus. The selective expression of cytostatin I was demonstrated during analysis expression in selected human tissues. The cytostatin I gene was found three times in nine week old early stage library, it was found once each in breast lympho node library, pancreas library and tonsils library. Cytostatin I protein was expressed and purified from E. coli. Our findings demonstrate that cytostatin I has growth inhibitory activity against breast cancer cells, leukemia cells, fibroblast cells, and endothelial cells.

BRIEF DESCRIPTION OF DRAWINGS

FIG. 1. Nucleotide and amino acid sequence of human Cytostatin I

The nucleotide sequence of the cDNA encoding human cytostatin (SEQ ID NO:1) and amino acid sequence (SEQ ID NO:2) is shown. The cDNA sequence encodes a primary translation product of 107 amino acids of which the first 21 to 38 amino acids likely represent a putative leader sequence or transmembrane domain.

Figure 2B:
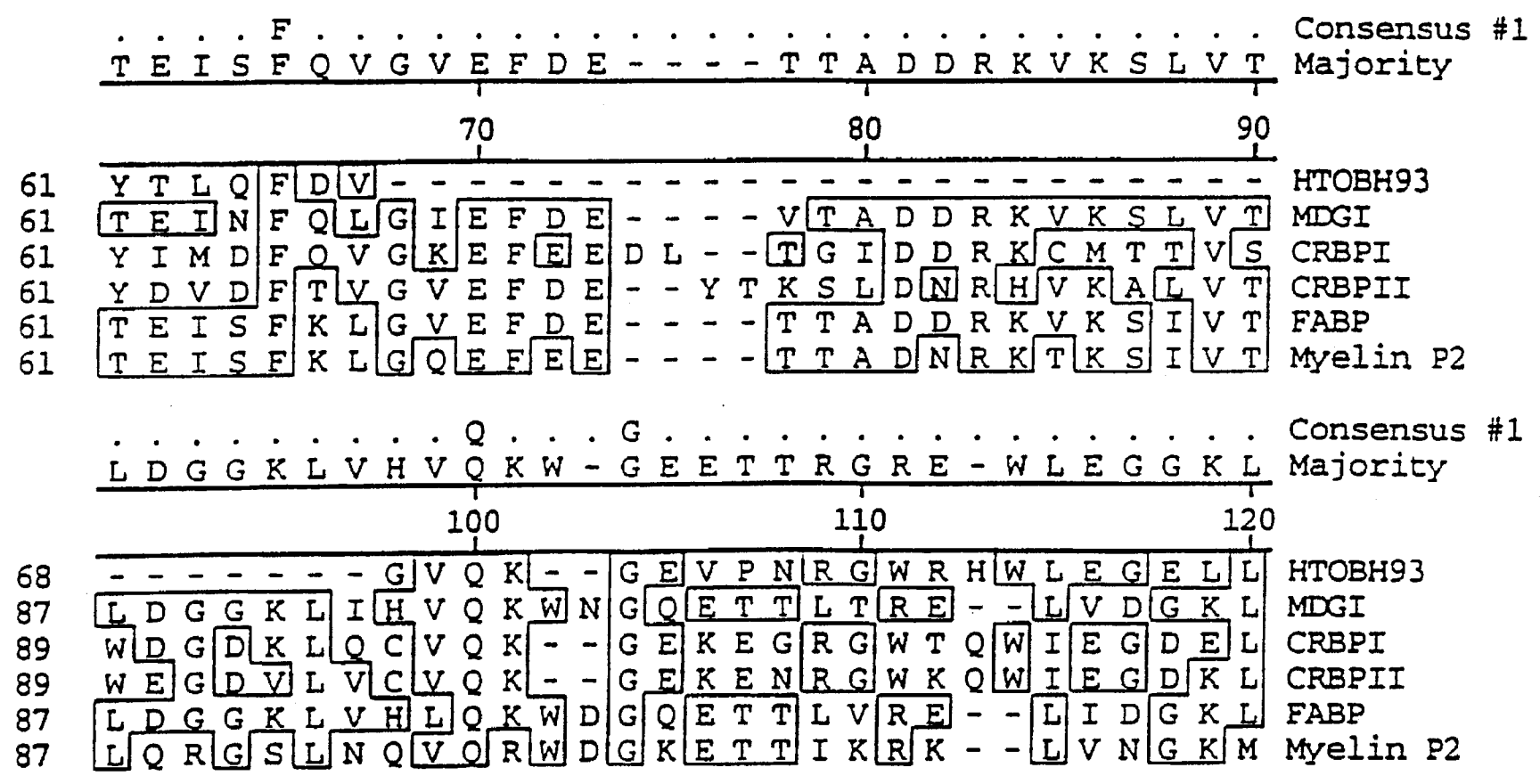

FIGS. 2A to 2C. Sequence homology of Cytostatin I with other family members.

Comparison of the amino acid sequence of cytostatin I (HTOBH93, top) to other members in the family is shown.

Figure 3A:
Figure 3B:
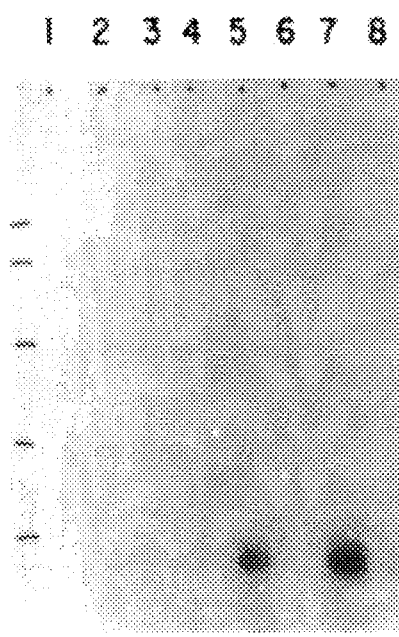
Figure 3C:
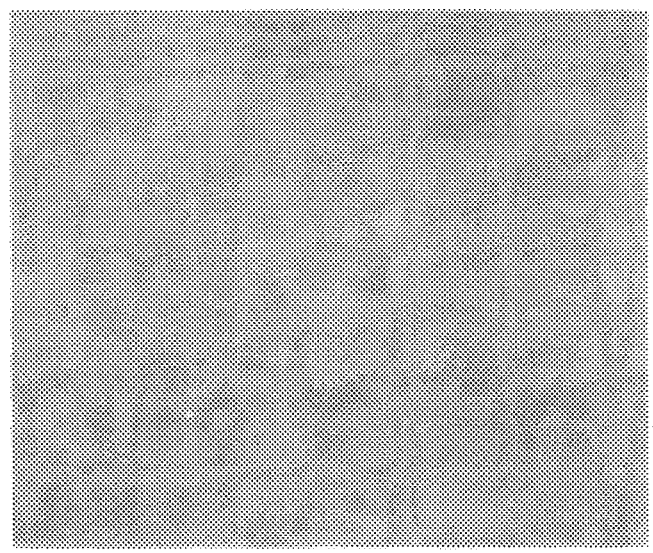

FIGS. 3A to 3C. Tissue distribution of cytostatin I.

(3A & 3B) Two µg of polyA RNA from the human tissues indicated were separated on a 1% agarose-formaldehyde gel and transferred to a nylon membrane. The membrane was probed with $^{32}$P-labeled cytostatin I cDNA probe. Cytostatin I is highly expressed in spleen and kidney, moderately expressed in liver and thymus. The lanes on the 3A and 3B gels are:

| FIG. 3A | FIG. 3B |
| --- | --- |
| Lane 1, spleen | heart |
| Lane 2, thymus | brain |
| Lane 3, prostate | placenta |
| Lane 4, testis | lung |
| Lane 5, ovary | liver |
| Lane 6, small intestinal | skeletal muscle |
| Lane 7, colon | kidney |
| Lane 8, peripheral blood leukocytes | pancreas |

RNA size marker (kb): 9.5; 7.5; 4.4; 2.4; 1.35.

3C.) 10 µg of total RNA from the cell lines shown were separated on a 1% agarose-formaldehyde gel and transferred to a nylon membrane. The membrane was probed with $^{32}$P-labeled cytostatin I cDNA. Lane 1, CAMA1 (breast cancer); Lane 2 AN3CA (uterine cancer); Lane 3, SK.UT.1 (uterine cancer); Lane 4, MG63 (osteoblastoma); Lane 5, HOS (osteoblastoma); Lane 6, MCF7 (breast cancer); Lane 7, OVCAR-3 (ovarian cancer); Lane 8, CAOV-3 (ovarian cancer); Lane 9, HUVEC; Lane 10, AOSMIC (smooth muscle); Lane 11, Fore skin fibroblast. The expression of cystatin I is undetectable in these cells.

FIG. 4

Purification of bacterial-expressed human cytostatin I (HG07400-2E).

The entire coding sequence including the putative signal sequence or transmembrane domain was fused in frame with a 6-His tag present in the expression vector pQE9 (Qiagen). E. coli harboring the expression plasmid were induced with 1 mM IPTG during the logarithmic growth phase. Following a 3-hour induction, the cell pellet was lysed with 6M Guanidine hydrochloride and cytostatin I was purified using a Nickel-chelate affinity chromatography column. The highly purified protein was denatured by dialysis in PBS buffer. M, molecular weight markers; Lane 1 and 2, induced cell lysate; Lane 3 and 4, uninduced cell lysate; Lane 5, pass through fraction from Nickel-chelate column purification; Lane 6, 7 and 8, Fraction eluted with 6M Guanidine hydrochloride (pH 5); 9 Fraction eluted with 6M Guanidine hydrochloride (pH 2).

FIG. 5A–E

5A Growth inhibitory activity of cytostatin I (HG07400-1E, highest concentration 100 ng/ml) against Mdamb 231 human breast cancer cells.

5B Growth inhibitory activity of cytostatin I (HG07400-2E, highest concentration 1000 ng/ml) against Mdamb 231 human breast cancer cells.

5C Growth inhibitory activity of cytostatin I (HG07400-1E) against Jurat human T cell leukemia cells.

5D Growth inhibitory activity of cytostatin I (HG07400-2E) against CCD-29LU human lung fibroblast cells.

5E Growth inhibitory activity of cytostatin I (HG07400-2E) against CPA 47 bovine pulmonary artery endothelial cells.

In accordance with an aspect of the present invention, there is provided an isolated nucleic acid (polynucleotide) which encodes for the mature polypeptide having the deduced amino acid sequence of FIG. 1 (SEQ ID NO:2) or for the mature cytostaatin I polypeptide encoded by the cDNA of the clone deposited with the American Type Culture Collection as ATCC Deposit No. 97103 on Mar. 21, 1995. In accordance with MPEP 608.01(p), all restrictions on the availability to the public of the deposited clone will be irrevocably removed upon the granting of a patent.

A polynucleotide encoding a cytostatin I of the present invention may be obtained from various human tissues, particularly nine week embryonic tissue, breast lymph node, pancreas, spleen, kidney, liver, thymus and tonsils. The polynucleotide of this invention was discovered in a cDNA library derived from human tonsils. It is structurally related to: 1) the mammary-derived growth inhibitor (MDGI) family; 2) the heart-fatty acid binding protein (FABP) family; 3) myelin P2 differentiation protein; 4) gastropropin; and 5) the cellular retinoic acid-binding protein (CRABP). It contains an open reading frame encoding a protein of about 107 amino acid residues. The protein exhibits the highest degree of homology to non human MDGI with 33% identity and 63% similarity to mouse MDGI. It is also important that cytostatin I is highly expressed in spleen and kidney, and moderately expressed in liver and thymus. There are 18 highly concerved amino acids in cytostatin I when compared to other polypeptides with amino sequence similarity. The most conserved sequence is the sequence between amino acids 54 and 60 where 5 of 7 amino acids are highly conserved.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIG. 1 (SEQ ID NO:1) or that of the deposited clone or may be a different coding sequence which coding sequence, as a result of the redundancy or degeneracy of the genetic code, encodes the same mature polypeptide as the DNA of FIG. 1 (SEQ ID NO:1) or the deposited cDNA.

The polynucleotide which encodes for the mature polypeptide of FIG. 1 (SEQ ID NO:2) or for the mature polypeptide encoded by the deposited cDNA may include, but is not limited to: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIG. 1 (SEQ ID NO:2) or the polypeptide encoded by the cDNA of the deposited clone. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIG. 1 (SEQ ID NO:2) or the same mature polypeptide encoded by the cDNA of the deposited clone as well as variants of such polynucleotides which variants encode for a fragment, derivative or analog of the polypeptide of FIG. 1 (SEQ ID NO:2) or the polypeptide encoded by the cDNA of the deposited clone. Such nucleotide variants include deletion variants, substitution variants and addition or insertion variants.

As hereinabove indicated, the cytostatin I polynucleotide may have a coding sequence which is a naturally occurring allelic variant of the coding sequence shown in FIG. 1 (SEQ ID NO:1) or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The present invention also includes polynucleotides, wherein the coding sequence for the mature cytostatin I polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. Thus, for example, the polynucleotide of the present invention may encode for a mature protein, or for a protein having a prosequence or for a protein having both a prosequence and a presequence (leader sequence).

The polynucleotides of the present invention may also have the coding sequence fused in frame to a marker sequence which allows for purification of the polypeptide of the present invention. The marker sequence may be a hexahistidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The present invention further relates to polynucleotides which hybridize to the hereinabove-described sequences if there is at least 50% and preferably 70% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which retain substantially the same biological function or activity as the mature polypeptide encoded by the cDNA of FIG. 1 (SEQ ID NO:1) or the deposited cDNA.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to a cytostatin I polypeptide which has the deduced amino acid sequence of FIG. 1 (SEQ ID NO:2) or which has the amino acid sequence encoded by the deposited cDNA, as well as fragments, analogs and derivatives of such polypeptide.

The terms "fragment," "derivative" and "analog" when referring to the polypeptide of FIG. 1 (SEQ ID NO:2) or that encoded by the deposited cDNA, means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of FIG. 1 (SEQ ID NO:2) or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the cytostatin I genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the E. coli. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in E. coli.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as E. coli, Streptomyces, Salmonella typhimurium; fungal cells, such as yeast; insect cells such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example; Bacterial: pQE70, pQE60, pQE-9 (Qiagen), pBS, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia); Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for Use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), a-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The cytostatin I polypeptide can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The cytostatin I polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The medical relevance and practical use of the cytostatin I of the present invention are based upon comparisons with other known proteins and by experimental analysis. The experimental results suggest that cytostatin I, as a therapeutic protein, may have the following medical applications:
1. Anti-tumor: the growth inhibitory activity of cytostatin I may be used as a therapeutic agent to treat various cancers.
2. Anti-angiogenesis: cytostatin I inhibiting fibroblast and endothelial cell growth.
3. Anti-metastasis: tumor cells must attract new vessels in order to grow and metastasize efficiently.
4. Stimulation of milk production after childbirth: cytostatin I inhibits mammary epithelial cell growth and modulation mammary gland differentiation, promotes formation of alveolar buds, supports development of differentiated lobuloalveoli, and stimulates milk protein synthesis and fat droplet accumulation.
5. Promoting involution of breast (return of an enlarged breast to normal size after parturition, childbirth): Antisense phosphorothioate oligonucleotides or antibodies to cytostatin I could selective inhibition of endogenous cytostatin I expression in mammary epithelial cells and suppresses appearance of alveolar end buds and lowers the beta-casein level.
6. Stimulation of dairy cows milk production or recombinant proteins produced by cows.
7. Modulation of beta-adrenergic sensitivity of cardiac myocytes.

The various potential therapeutic catagories and uses of the cytostatin I include but are not limited to all aspects of the following areas of medical practice: 1. Oncology, 2, Cardiovascular, 3). Immunology, 4. Hematology, 5. Metabolism, 6. Gynecology and Obstetrics, and 7. Endocrinology.

Fragments of the full length cytostatin I gene may be used as a hybridization probe for a cDNA library to isolate the full length cytostatin I gene and to isolate other genes which have a high sequence similarity to the cytostatin I gene or similar biological activity. Probes of this type generally have at least 20 bases. Preferably, however, the probes have at least 30 bases and generally do not exceed 50 bases, although they may have a greater number of bases. The probe may also be used to identify a cDNA clone corresponding to a full length transcript and a genomic clone or clones that contain the complete cytostatin I gene including regulatory and promotor regions, exons, and introns. An example of a screen comprises isolating the coding region of the cytostatin I gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The polynucleotides and polypeptides of the present invention may be employed as research reagents and materials for discovery of treatments and diagnostics to human disease.

This invention provides a method for identification of the receptor for the human cytostatin I ligand. The gene encoding the receptor can be identified by numerous methods known to those of skill in the art, for example, ligand panning and FACS sorting (Coligan, et al., Current Protocols in Immun., 1(2), Chapter 5, (1991)). Preferably, expression cloning is employed wherein polyadenylated RNA is prepared from a cell responsive to the cytostatin I ligand, and a cDNA library created from this RNA is divided into pools and used to transfect COS cells or other cells that are not responsive to the cytostatin I ligand. Transfected cells which are grown on glass slides are exposed to labeled cytostatin I ligand. The cytostatin I ligand can be labeled by a variety of means including iodination or inclusion of a recognition site for a site-specific protein kinase. Following fixation and incubation, the slides are subjected to auto-radiographic analysis. Positive pools are identified and sub-pools are prepared and re-transfected using an iterative sub-pooling and re-screening process, eventually yielding a single clone that encodes the putative receptor. As an alternative approach for receptor identification, labeled ligand can be photoaffinity linked with cell membrane or extract preparations that express the receptor molecule. Cross-linked material is resolved by PAGE and exposed to X-ray film. The labeled complex containing the ligand-receptor can be excised, resolved into peptide fragments, and subjected to protein microsequencing. The amino acid sequence obtained from microsequencing would be used to design a set of degenerate oligonucleotide probes to screen a cDNA library to identify the gene encoding the putative receptor.

The method for determining whether a ligand can bind to the cytostatin I receptor comprises transfecting a cell population (one presumed not to contain the receptor) with the appropriate vector expressing the cytostatin I receptor, such that the cell will now express the cytostatin I receptor. A suitable response system is obtained by transfection of the DNA into a suitable host containing the desired second messenger pathways including cAMP, ion channels, phosphoinositide kinase, or calcium response. Such a transfection system provides a response system to analyze the activity of various ligands exposed to the cell. Ligands chosen could be identified through a rational approach by taking known ligands that interact with similar types of receptors or using small molecules, cell supernatants or extracts or natural products.

This invention provides a method of screening drugs to identify those which enhance (agonists) or block (antagonists) interaction of ligand to receptor. An agonist is a compound which increases the natural biological functions of cytostatin I, while antagonists eliminate such functions. As an example, a mammalian cell or membrane preparation expressing the cytostatin I receptor would be incubated with labeled ligand in the presence of the drug. The ability of the drug to enhance or block this interaction could then be measured. Alternatively, the response of a known second messenger system following interaction of ligand and receptor would be measured and compared in the presence or absence of the drug. Such second messenger systems include but are not limited to, cAMP guanylate cyclase, ion channels or phosphoinositide hydrolysis. (The present invention also relates to an assay for identifying potential antagonist specific to cytostatin I. An example of such an assay combines cytostatin I and a potential antagonist with membrane-bound cytostatin I receptors or recombinant cytostatin I under appropriate conditions for a competitive inhibition assay. Cytostatin I can be labeled, such as by radio activity, such that the number of cytostatin molecules bound to the receptor can determine the effectiveness of the potential antagonist.

Potential antagonists include an antibody, or in some cases, an oligopeptide, which binds to the polypeptide. Alternatively, a potential antagonist may be a closely related protein which binds to the receptor sites, however, they are inactive forms of the polypeptide and thereby prevent the action of cytostatin I since receptor sites are occupied.

Another potential antagonist is an antisense construct prepared using antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res., 6:3073 (1979); Cooney et al, Science, 241:456 (1988); and Dervan et al., Science, 251: 1360 (1991)), thereby preventing transcription and the production of cytostatin I. The antisense RNA oligonucleotide hybridizes to the mRNA in vivo and blocks translation of the mRNA molecule into cytostatin I polypeptide (Antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of cytostatin I.

Potential antagonists include a small molecule which binds to and occupies the receptor binding site of the cytostatin I polypeptide thereby making the binding site inaccessible to receptor such that normal biological activity is prevented. Examples of small molecules include but are not limited to small peptides or peptide-like molecules.

The antagonists may be employed to treat disease conditions caused by excess cytostatin I production or activity. The antagonists may be employed in a composition with a pharmaceutically acceptable carrier, e.g., as hereinafter described.

The polypeptides of the present invention may be employed in combination with a suitable pharmaceutical carrier. Such compositions comprise a therapeutically effective amount of the polypeptide, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

The pharmaceutical compositions may be administered in a convenient manner such as by the oral (when protected from hydrolysis or digestion), topical, intravenous, intraperitoneal, intramuscular, subcutaneous, intranasal or intradermal routes. The pharmaceutical compositions are administered in an amount which is effective for treating and/or prophylaxis of the specific indication. In general, they are administered in an amount of at least about 10 µg/kg body weight and in most cases they will be administered in an amount not in excess of about 8 mg/Kg body weight per day. In most cases, the dosage is from about 10 µg/kg to about 1 mg/kg body weight daily, taking into account the routes of administration, symptoms, etc.

The cytostatin I polypeptides and agonists and antagonists which are polypeptides may also be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art and are apparent from the teachings herein. For example, cells may be engineered by the use of a retroviral plasmid vector containing RNA encoding a polypeptide of the present invention.

Similarly, cells may be engineered in vivo for expression of a polypeptide in vivo by, for example, procedures known in the art. For example, a packaging cell is transduced with a retroviral plasmid vector containing RNA encoding a polypeptide of the present invention such that the packaging cell now produces infectious viral particles containing the gene of interest. These producer cells may be administered to a patient for engineering cells in vivo and expression of the polypeptide in vivo. These and other methods for administering a polypeptide of the present invention by such method should be apparent to those skilled in the art from the teachings of the present invention.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, arian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., Biotechniques, Vol. 7, No. 9, 980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or hetorologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, _-2, _-AM, PA12, T19-14X, VT-19-17-H2, _CRE, _CRIP, GP+E-86, GP+envAm12, and DAN cell lines as described in Miller, Human Gene Therapy, Vol. 1, pgs. 5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

This invention is also related to the use of the cytostatin I gene as a diagnostic. Detection of a mutated form of cytostatin I will allow a diagnosis of a disease or a susceptibility to a disease which results from underexpression of cytostatin I for example, failure to properly inhibit growth of a tumor cell.

Individuals carrying mutations in the human cytostatin I gene may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR (Saiki et al., Nature, 324:163–166 (1986)) prior to analysis. RNA or cDNA may also be used for the same purpose. As an example, PCR primers complementary to the nucleic acid encoding cytostatin I can be used to identify and analyze cytostatin I mutations. For example, deletions and insertions can be detected by a change in size of the amplified product in comparison to the normal genotype. Point mutations can be identified by hybridizing amplified DNA to radiolabeled cytostatin I RNA or alternatively, radiolabeled cytostatin I antisense DNA sequences. Perfectly matched sequences can be distinguished from mismatched duplexes by RNase A digestion or by differences in melting temperatures.

Sequence differences between the reference gene and genes having mutations may be revealed by the direct DNA sequencing method. In addition, cloned DNA segments may be employed as probes to detect specific DNA segments. The sensitivity of this method is greatly enhanced when combined with PCR. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230:1242 (1985)).

Sequence changes at specific locations may also be revealed by nuclease protection assays, such as RNase and S1 protection or the chemical cleavage method (e.g., Cotton et al., PNAS, USA, 85:4397–4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The present invention also relates to a diagnostic assay for detecting altered levels of cytostatin I protein in various tissues since an over-expression of the proteins compared to normal control tissue samples can detect the presence of cytostatin I. Assays used to detect levels of cytostatin I protein in a sample derived from a host are well-known to those of skill in the art and include radioimmunoassays, competitive-binding assays, Western Blot analysis and preferably an ELISA assay. An Elisa assay initially comprises preparing an antibody specific to the cytostatin I antigen, preferably a monoclonal antibody. In addition a reporter antibody is prepared against the monoclonal antibody. To the reporter antibody is attached a detectable reagent such as radioactivity, fluorescence or in this example a horseradish peroxidase enzyme. A sample is now removed from a host and incubated on a solid support, e.g. a polystyrene dish, that binds the proteins in the sample. Any free protein binding sites on the dish are then covered by incubating with a non-specific protein such as bovine serum albumin. Next, the monoclonal antibody is incubated in the dish during which time the monoclonal antibodies attach to any cytostatin I proteins attached to the polystyrene dish. All unbound monoclonal antibody is washed out with buffer. The reporter antibody linked to horseradish peroxidase is now placed in the dish resulting in binding of the reporter antibody to any monoclonal antibody bound to cytostatin I. Unattached reporter antibody is then washed out. Peroxidase substrates are then added to the dish and the amount of color developed in a given time period is a measurement of the amount of cytostatin I protein present in a given volume of patient sample when compared against a standard curve.

A competition assay may be employed wherein antibodies specific to cytostatin I is attached to a solid support and labeled cytostatin I and a sample derived from the host are passed over the solid support and the amount of label detected attached to the solid support can be correlated to a quantity of cytostatin I in the sample.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 500 or 600 bases; however, clones larger than 2,000 bp have a higher likelihood of binding to a unique chromosomal location with sufficient signal intensity for simple detection. FISH requires use of the clones from which the express sequence tag (EST) was derived, and the longer the better. For example, 2,000 bp is good, 4,000 is better, and more than 4,000 is probably not necessary to get good results a reasonable percentage of the time. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 μg of plasmid or DNA fragment is used with about 2 units of enzyme in about 20 μl of buffer, solution. For the purpose of isolating DNA fragments for plasmid construction, typically 5 to 50 μg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units of T4 DNA ligase ("ligase") per 0.5 μg of approximately equimolar amounts of the DNA fragments to be ligated.

Unless otherwise stated, transformation was performed as described in the method of Graham, F. and Van der Eb, A., Virology, 52:456–457 (1973).

EXAMPLE 1

Bacterial Expression and Purification of Cytostatin I

The DNA sequence encoding cytostatin I, ATCC #97103, is initially amplified using PCR oligonucleotide primers corresponding to the 5' sequences of the processed cytostatin I protein (minus the signal peptide sequence) and the vector sequences 3' to the cytostatin I gene. Additional nucleotides corresponding to the primers used were added to the 5' and 3' sequences respectively. The 5' oligonucleotide primer has the sequence 5'CGCGGATCCATGCCTCCCAACCT-CACTG 3' (SEQ ID NO:3) and contains a BamHI restriction enzyme site followed by 19 nucleotides of cytostatin I coding sequence starting from the starting codon of the gene. The 3' sequence 5'GCGTCTAGACTATCTGACCTTCCT-GAAGAC3' (SEQ ID NO:4) contains complementary sequences to XbaI site and is followed by 20 nucleotides of cytostatin I including a stop codon. The restriction enzyme sites correspond to the restriction enzyme sites on the bacterial expression vector pQE-9. (Qiagen, Inc. 9259 Eton Avenue, Chatsworth, Calif., 91311). pQE-9 encodes antibiotic resistance (Amp$^r$), a bacterial origin of replication (ori), an IPTG-regulatable promoter operator (P/O), a ribosome binding site (RBS), a 6-His tag and restriction enzyme sites. pQE-9 was then digested with BamHI and XbaI. The amplified sequences were ligated into pQE-9 and were inserted in frame with the sequence encoding for the histidine tag and the RBS. The ligation mixture was then used to transform E. coli strain M15 available from Qiagen under the trademark M15/rep 4 by the procedure described in Sambrook, J. et al., Molecular Cloning: A Laboratory Manual, Cold Spring Laboratory Press, (1989). M15/rep4 contains multiple copies of the plasmid pREP4, which expresses the lacI repressor and also confers kanamycin resistance (Kan$^r$). Transformants are identified by their ability to grow on LB plates and ampicillin/kanamycin resistant colonies were selected. Plasmid DNA was isolated and confirmed by restriction analysis. Clones containing the desired constructs were grown overnight (O/N) in liquid culture in LB media supplemented with both Amp (100 ug/ml) and Kan (25 ug/ml). The O/N culture is used to inoculate a large culture at a ratio of 1:100 to 1:250. The cells were grown to an optical density 600 (O.D.$^{600}$) of between 0.4 and 0.6. IPTG ("Isopropyl-B-D-thiogalacto pyranoside") was then added to a final concentration of 1 mM. IPTG induces by inactivating the lacI repressor, clearing the P/O leading to increased gene expression. Cells were grown an extra 3 to 4 hours. Cells were then harvested by centrifugation. The cell pellet was solubilized in the chaotropic agent 6 Molar Guanidine HCl. After clarification, solubilized cytostatin I was purified from this solution by chromatography on a Nickel-Chelate column under conditions that allow for tight binding by proteins containing the 6-His tag (Hochuli, E. et al., J. Chromatography 411:177–184 (1984)). Cytostatin I (90% pure) was eluted from the column in 6 molar guanidine HCl pH 5.0 and for the purpose of renaturation adjusted to 3 molar guanidine HCl, 100 mM sodium phosphate, 10 mmolar glutathione (reduced) and 2 mmolar glutathione (oxidized). After incubation in this solution for 12 hours the protein was dialyzed to 10 mmolar sodium phosphate.

Figure 4:
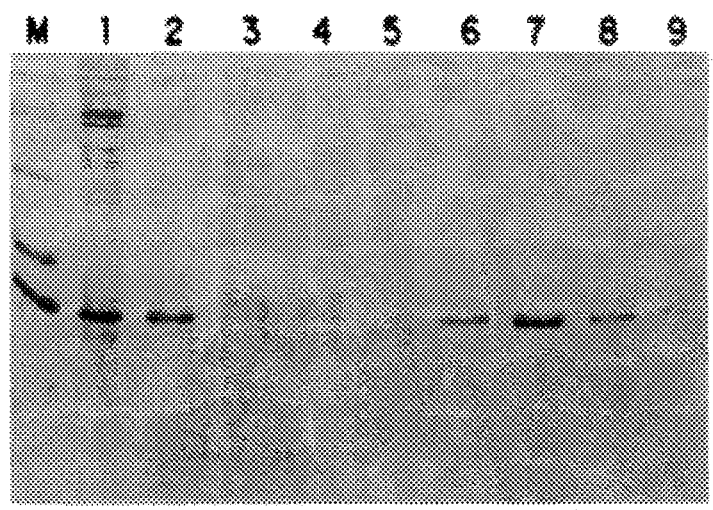
Figure 5A:
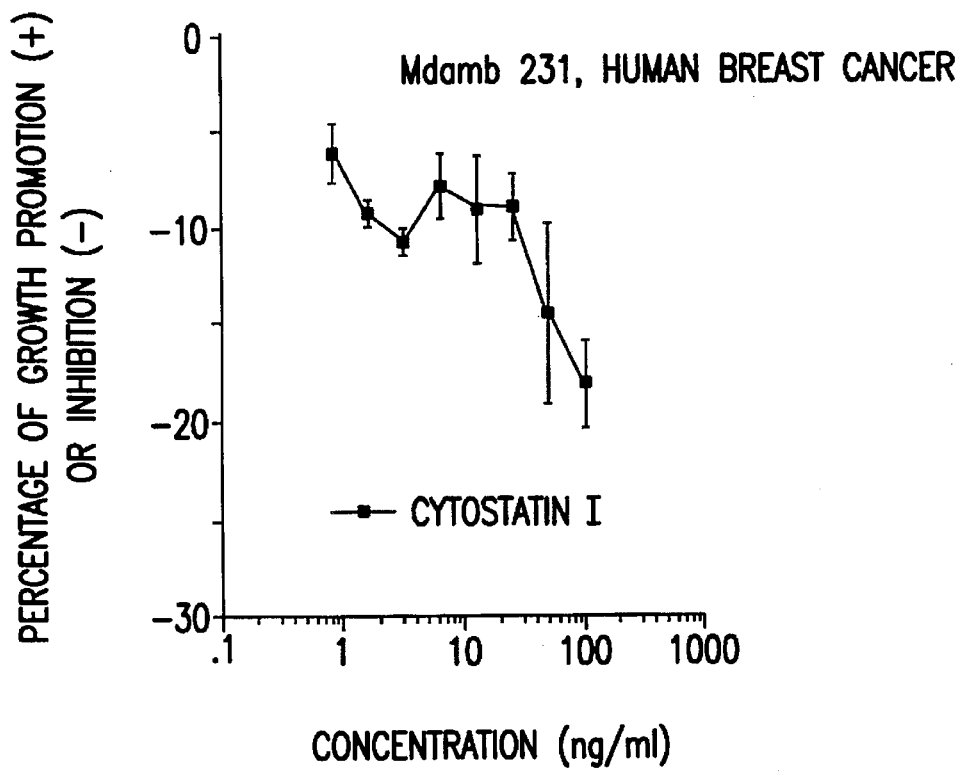
Figure 5B:
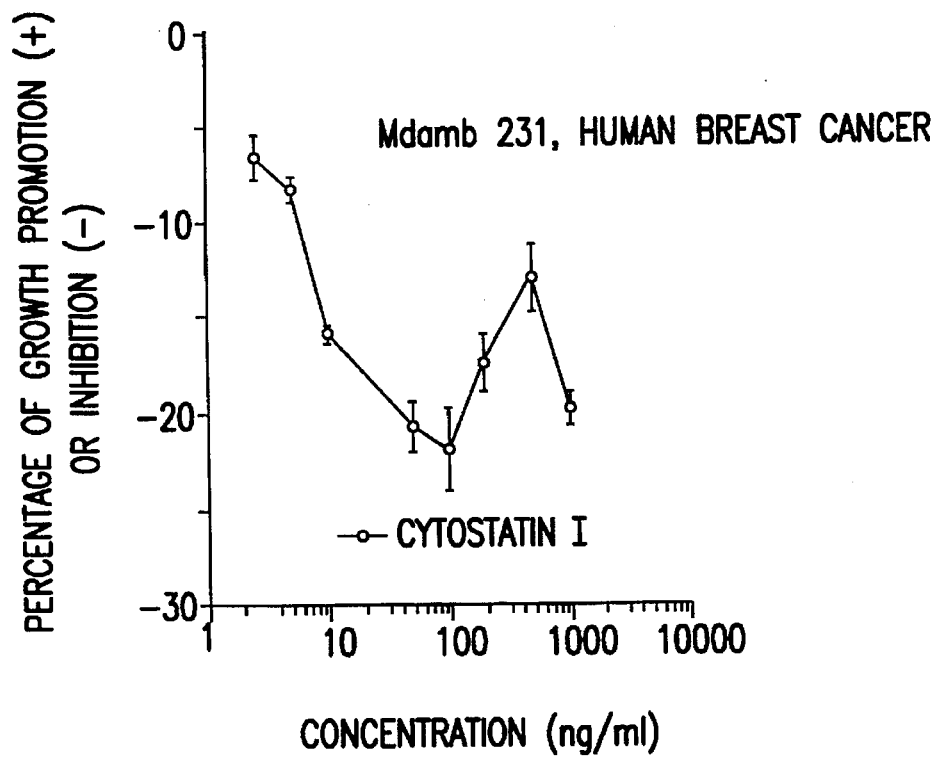
Figure 5C:
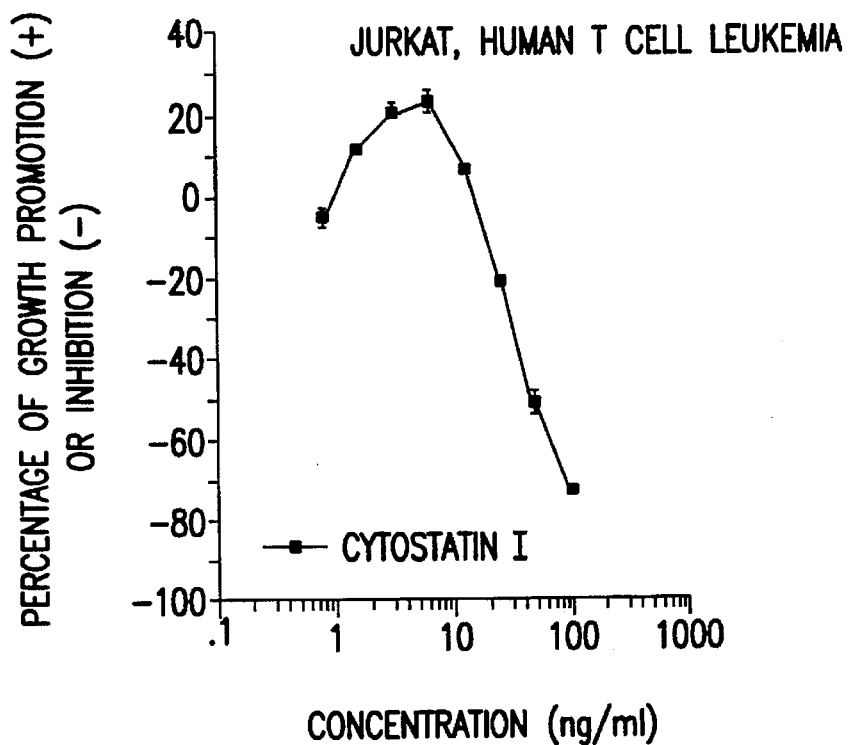
Figure 5D:
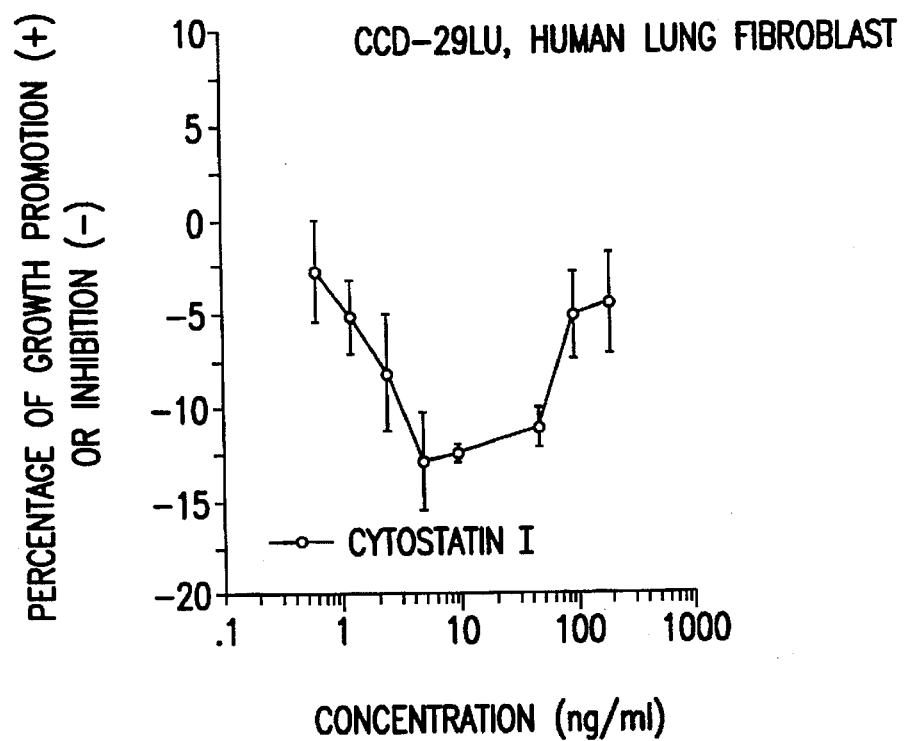
Figure 5E:
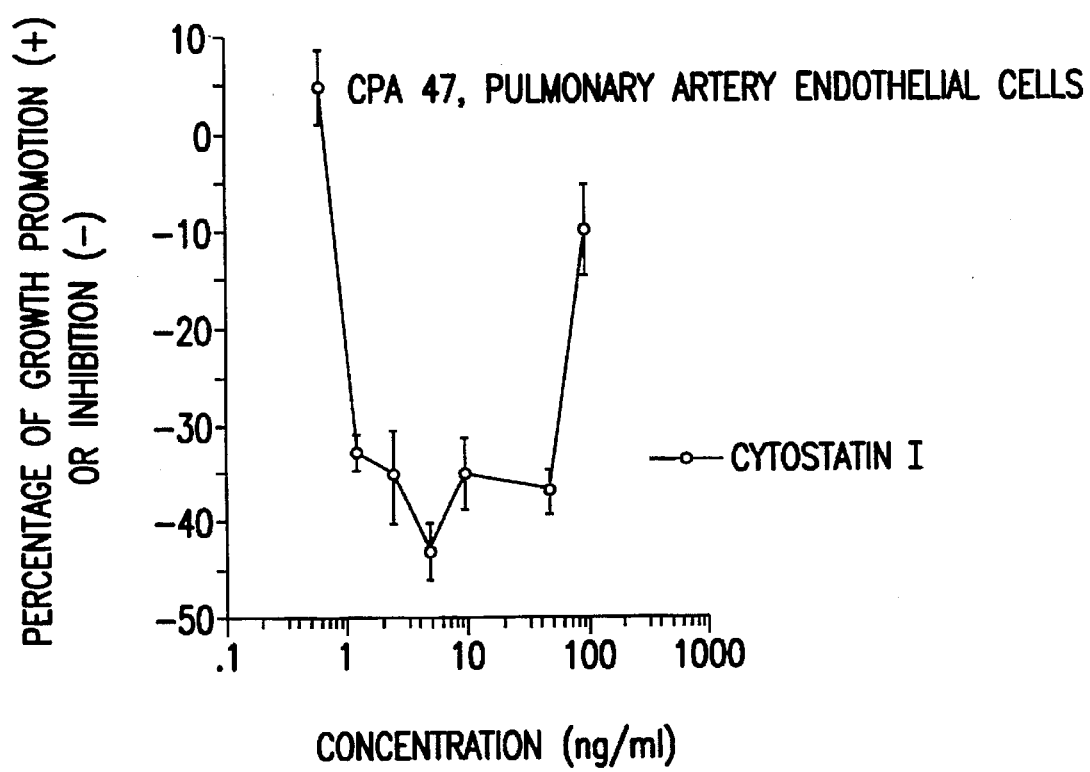

The entire coding sequence including the putative signal sequence or transmembrane domain was fused in frame with a 6-His tag present in the expression vector pQE9 (Qiagen). E. coli harboring the expression plasmid were induced with 1 mM IPTG during the logarithmic growth phase. Following a 3-hour induction, the cell pellet was lysed with 6M Guanidine hydrochloride and cytostatin I was purified using a Nickel-chelate affinity chromatography column. The highly purified protein was denatured by dialysis in PBS buffer. The gel is shown in FIG. 4: M, molecular weight markers; Lane 1 and 2, induced cell lysate; Lane 3 and 4, uninduced cell lysate; Lane 5, pass through fraction from Nickel-chelate column purification; Lane 6, 7 and 8, Fraction eluted with 6M Guanidine hydrochloride (pH 5); 9 Fraction eluted with 6M Guanidine hydrochloride (pH 2).

EXAMPLE 2

Cloning and Expression of Cytostatin I Using the Baculovirus Expression System The DNA sequence encoding the full length cytostatin I protein, ATCC #97103, was amplified using PCR oligonucleotide primers corresponding to the 5' and 3' sequences of the gene:

The 5' primer has the sequence CGC GGA TCC CCC TCC CAA CCT CAC TGG CTA C (SEQ ID NO:5) and contains a BamHI restriction enzyme site (in bold) followed by 22 nucleotides. The 3' primer has the sequence CGC GGA TCC CTA TCT GAC CTT CCT GAA GA (SEQ ID NO:6) and contains the cleavage site for the restriction endonuclease BanHi and 20 nucleotides of the C-terminal coding sequence including a stop codon. The amplified sequences were isolated from a 1% agarose gel using a commercially available kit ("Geneclean," BIO 101 Inc., La Jolla, Calif.). The fragment was then digested with the endonuclease BamHI and then purified again on a 1% agarose gel. This fragment is designated F2.

The vector pA2-Gp (modification of pVL941 vector, discussed below) is used for the expression of the cytostatin I protein using the baculovirus expression system (for review see: Summers, M. D. and Smith, G. E. 1987, A manual of methods for baculovirus vectors and insect cell culture procedures, Texas Agricultural Experimental Station Bulletin No. 1555). This expression vector contains the strong polyhedrin promoter of the Autographa californica nuclear polyhedrosis virus (AcMNPV) followed by the recognition sites for the restriction endonucleases BamHI. The polyadenylation site of the simian virus (SV) 40 is used for efficient polyadenylation. For an easy selection of recombinant virus the beta-galactosidase gene from E. coli is inserted in the same orientation as the polyhedrin promoter followed by the polyadenylation signal of the polyhedrin gene. The polyhedrin sequences are flanked at both sides by viral sequences for the cell-mediated homologous recombination of co-transfected wild-type vital DNA. Many other baculovirus vectors could be used in place of pRG1 such as pac373, pVL941 and pAcIM1 (Luckow, V. A. and Summers, M. D., Virology, 170:31–39).

The plasmid was digested with the restriction enzymes BamHI and then dephosphorylated using calf intestinal phosphatase by procedures known in the art. The DNA was then isolated from a 1% agarose gel using the commercially available kit ("Geneclean" BIO 101 Inc., La Jolla, Calif.). This vector DNA is designated V2.

Fragment F2 and the dephosphorylated plasmid V2 were ligated with T4 DNA ligase. E.coli HB101 cells were then transformed and bacteria identified that contained the plasmid (pBac-cytostatin I) with the cytostatin I gene using the enzyme BamHI. The sequence of the cloned fragment was confirmed by DNA sequencing.

5 μg of the plasmid pBac-cytostatin I was co-transfected with 1.0 μg of a commercially available linearized baculovirus ("BaculoGold™ baculovirus DNA", Pharmingen, San Diego, Calif.) using the lipofection method (Felgner et al. Proc. Natl. Acad. Sci. USA, 84:7413–7417 (1987)).

1 µg of BaculoGold™ virus DNA and 5 µg of the plasmid pBac-cytostatin I were mixed in a sterile well of a microtiter plate containing 50 µl of serum free Grace's medium (Life Technologies Inc., Gaithersburg, Md.). Afterwards 10 µl Lipofectin plus 90 µl Grace's medium were added, mixed and incubated for 15 minutes at room temperature. Then the transfection mixture was added dropwise to the Sf9 insect cells (ATCC CRL 1711) seeded in a 35 mm tissue culture plate with 1 ml Grace's medium without serum. The plate was rocked back and forth to mix the newly added solution. The plate was then incubated for 5 hours at 27° C. After 5 hours the transfection solution was removed from the plate and 1 ml of Grace's insect medium supplemented with 10% fetal calf serum was added. The plate was put back into an incubator and cultivation continued at 27° C. for four days.

After four days the supernatant was collected and a plaque assay performed similar as described by Summers and Smith (supra). As a modification an agarose gel with "Blue Gal" (Life Technologies Inc., Gaithersburg) was used which allows an easy isolation of blue stained plaques. (A detailed description of a "plaque assay" can also be found in the user's guide for insect cell culture and baculovirology distributed by Life Technologies Inc., Gaithersburg, page 9–10) .

Four days after the serial dilution, the virus was added to the cells, blue stained plaques were picked with the tip of an Eppendorf pipette. The agar containing the recombinant viruses was then resuspended in an Eppendorf tube containing 200 µl of Grace's medium. The agar was removed by a brief centrifugation and the supernatant containing the recombinant baculovirus was used to infect Sf9 cells seeded in 35 mm dishes. Four days later the supernatants of these culture dishes were harvested and then stored at 4° C.

Sf9 cells were grown in Grace's medium supplemented with 10% heat-inactivated FBS. The cells were infected with the recombinant baculovirus V-cytostatin I at a multiplicity of infection (MOI) of 2. Six hours later the medium was removed and replaced with SF900 II medium minus methionine and cysteine (Life Technologies Inc., Gaithersburg). 42 hours later 5 µCi of $^{35}$S-methionine and 5 µCi $^{35}$S cysteine (Amersham) were added. The cells were further incubated for 16 hours before they were harvested by centrifugation and the labelled proteins visualized by SDS-PAGE and autoradiography (FIG. 4).

EXAMPLE 3

Expression of Recombinant Cytostatin I in COS Cells

The expression of plasmid containing the cytostatin I gene is derived from a vector pcDNAI/Amp (Invitrogen) containing: 1) SV40 origin of replication, 2) ampicillin resistance gene, 3) E.coli replication origin, 4) CMV promoter followed by a polylinker region, an SV40 intron and polyadenylation site. A DNA fragment encoding the entire cytostatin I precursor and a HA tag fused in frame to its 3' end is cloned into the polylinker region of the vector, therefore, the recombinant protein expression is directed under the CMV promoter. The HA tag corresponds to an epitope derived from the influenza hemagglutinin protein as previously described (I. Wilson, H. Niman, R. Heighten, A Cherenson, M. Connolly, and R. Lerner, 1984, Cell 37:767, (1984)). The infusion of HA tag to the target protein allows easy detection of the recombinant protein with an antibody that recognizes the HA epitope.

The plasmid construction strategy is described as follows:

The DNA sequence encoding cytostatin I, ATCC #97103, is constructed by PCR on the original cytostatin I cloned using two primers: the 5' primer from the 5' end of the cytostatin I gene and a 3' sequence from the 3' end of the cytostatin I gene. Therefore, the PCR product contains the acytostatin I coding sequence followed by HA tag fused in frame, a translation termination stop codon next to the HA tag, and a final restriction endonuclease site. The PCR amplified DNA fragment and the vector, pcDNAI/Amp, are digested with the appropriate restriction enzymes and ligated. The ligation mixture is transformed into E. coli strain SURE (available from Stratagene Cloning Systems, 11099 North Torrey Pines Road, La Jolla, Calif. 92037) the transformed culture is plated on ampicillin media plates and resistant colonies are selected. Plasmid DNA is isolated from transformants and examined by restriction analysis for the presence of the correct fragment. For expression of the recombinant cytostatin I, COS cells are transfected with the expression vector by DEAE-DEXTRAN method (J. Sambrook, E. Fritsch, T. Maniatis, Molecular Cloning: A Laboratory Manual, Cold Spring Laboratory Press, (1989)). The expression of the cytostatin I HA protein is detected by radiolabelling and immunoprecipitation method (E. Harlow, D. Lane, Antibodies: A Laboratory Manual, Cold Spring Harbor Laboratory Press, (1988)). Cells are labelled for 8 hours with $^{35}$S-cysteine two days post transfection. Culture media is then collected and cells are lysed with detergent (RIPA buffer (150 mM NaCl, 1% NP-40, 0.1% SDS, 1% NP-40, 0.5% DOC, 50 mM Tris, pH 7.5) (Wilson, I. et al., Id. 37:767 (1984)). Both cell lysate and culture media are precipitated with an HA specific monoclonal antibody. Proteins precipitated are analyzed on 15% SDS-PAGE gels.

EXAMPLE 4

Expression Pattern of Cytostatin I in Human Tissue

Northern blot analysis is carried out to examine the levels of expression of cytostatin I in human tissues. Total cellular RNA samples are isolated with RNAzol™ B system (Biotecx Laboratories, Inc. 6023 South Loop East, Houston, Tex. 77033). About 10 µg of total RNA isolated from each human tissue specified is separated on 1% agarose gel and blotted onto a nylon filter (Sambrook, Fritsch, and Maniatis, Molecular Cloning, Cold Spring Harbor Press, (1989)). The labeling reaction is done according to the Stratagene Prime-It kit with 50 ng DNA fragment. The labeled DNA is purified with a Select-G-50 column (5 Prime—3 Prime, Inc. 5603 Arapahoe Road, Boulder, Colo. 80303). The filter is then hybridized with radioactive labeled full length cytostatin I gene at 1,000,000 cpm/ml in 0.5M NaPO$_4$, pH 7.4 and 7% SDS overnight at 65° C. After washing twice at room temperature and twice at 60° C. with 0.5×SSC, 0.1% SDS, the filter is then exposed at −70° C. overnight with an intensifying screen. FIG. 3A issustrates the tissue distribution of cytostatin I in various human tissues. The results are issustrated in FIGS. 3A, 3B and 3C.

EXAMPLE 5

Biological Activity of Cytostatin I

The activity of cytostatin is illustrated in FIG. 5. Two-fold serial dilution of purified cytostatin I (MDGI homolog, HG07400-1E or HG07400-2E) starting from 100 ng/ml were made in RPMI 1640 medium with 0.5% FBS. The adherent target cells were prepared from confluent cultures by trypsinization in PBS, and non-adherent target cells were harvested from stationary cultures and washed once with medium. Target cells were suspended at $1\times10^5$ cells/ml in medium containing 0.5 % FBS, then 0.1 ml aliquots were dispensed into 96-well flat-bottomed microtiter plates containing 0.1 ml serially diluted test samples. Incubation was continued for 70 hr. The activity was quantified using MTS [3(4.5-dimethyl-thiazoyl-2-yl) 5 (3-carboxymethoxyphenyl) -2-(4-sulfophenyl)-2H -tetrazolium)] Assay. MTS assay is performed by the addition of 20 µl of MTS and phenazine methosulfate (PMS) solution to 96 well plates (Stock solution was prepared as described by Promega Technical Bulletin No. 169). During a 3 hr incubation, living cells convert the MTS into a the aqueous soluble formazan product. Wells with medium only (no cells) were processed in exactly the same manner as the rest of the wells and were used for blank controls. Wells with medium and cells were used as baseline controls. The absorbence at 490 nm was recorded using an ELISA reader and is proportional to the number of viable cells in the wells. Cell growth promotion (positive percentage) or inhibition (negative percentage), as a percentage compared to baseline control wells (variation between three baseline control well is less than 5%), calculated for each sample concentration, by the formula: $OD_{experimental}/OD_{baseline\ control} \times 100 - 100$. All determinations were made in triplicate. Mean and SD were calculated by Microsoft Excel.

EXAMPLE 6

Expression of Cytostatin I via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

A a selected vector such as Moloney murine leukemia virus is digested with the appropriate restriction endonuclease and subsequently treated with calf intestinal phosphatase. The linear vector is fractionated on agarose gel and purified, using glass beads.

A sub-fragment of the cytostatin I cDNA is isolated and the ends of this fragment are treated with DNA polymerase in order to fill in the recessed ends and create blunt ends. Known linkers are ligated to the blunt ends with T4 DNA ligase.

Equal quantities of the Moloney murine leukemia virus linear backbone and selected cytostatin I fragments are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector has the cytostatin I gene properly inserted.

Cytostatin I packaging cells are grown in tissue culture to confluent density in Dulbecco's Modified Eagles Medium (DMEM) with 10% calf serum (CS), penicillin and streptomycin. The expression vector containing the cytostatin I gene is then added to the media and the packaging cells are transduced with the vector. The packaging cells now produce infectious viral particles containing the cytostatin I gene (the packaging cells are now referred to as producer cells).

Fresh media is added to the transduced producer cells, and subsequently, media is harvested from a 10 cm plate of confluent producer cells. The spent media, containing the infectious vital particles, is filtered through a millipore filter to remove detached producer cells and this media is then used to infect fibroblast cells. Media is removed from a sub-confluent plate of fibroblasts and quickly replaced with the media from the producer cells After incubation this media is removed and replaced with fresh media. If the titer of virus is high, then virtually all fibroblasts will be infected and no selection is required. If the titer is very low, then it is necessary to use a retrovital vector that has a selectable marker, such as neo or his.

The engineered fibroblasts are then injected into the peritoneal cavity of rats, either alone or after having been grown to confluence on cytodex 3 microcarrier beads. The fibroblasts now produce the cytostatin I protein product.

Numerous modifications and variations of the present invention are possible in light of the above teachings and, therefore, within the scope of the appended claims, the invention may be practiced otherwise than as particularly described.

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
( A ) LENGTH: 861 base pairs
( B ) TYPE: nucleic acid
( C ) STRANDEDNESS: single
( D ) TOPOLOGY: linear (ii) MOLECULE TYPE: DNA (genomic)

(ix) FEATURE:
    (A) NAME/KEY: CDS
    (B) LOCATION: 94..414

(xi) SEQUENCE DESCRIPTION: SEQ ID NO:1:

```
CACGAGCTGG AATCTCTCAG CCTCACCTGC CAGACAACAC CCCCTCCTTC CTCACCCTGT      60

TTCCTGCATT CTCCTGAAAC CTTCATCCAC ACA ATG CCT CCC AAC CTC ACT GGC     114
                                     Met Pro Pro Asn Leu Thr Gly
                                      1               5

TAC TAC CGC TTT GTT TCG CAG AAG AAC ATG GAG GAC TAC CTG CAA GCC     162
Tyr Tyr Arg Phe Val Ser Gln Lys Asn Met Glu Asp Tyr Leu Gln Ala
         10                  15                  20

CTA AAC ATC AGC TTG GCT GTG CGG AAG ATC GCG CTG CTG CTG AAG CCG     210
Leu Asn Ile Ser Leu Ala Val Arg Lys Ile Ala Leu Leu Leu Lys Pro
     25                  30                  35

GAC AAG GAG ATC GAA CAC CAG GGC AAC CAC ATG ACG GTG AGG ACG CTC     258
Asp Lys Glu Ile Glu His Gln Gly Asn His Met Thr Val Arg Thr Leu
 40                  45                  50                  55

AGC ACC TTC CGA AAC TAC ACT TTG CAG TTT GAT GTG GGA GTG CAG AAA     306
Ser Thr Phe Arg Asn Tyr Thr Leu Gln Phe Asp Val Gly Val Gln Lys
             60                  65                  70

GGG GAG GTC CCC AAC CGG GGC TGG AGA CAC TGG CTG GAG GGA GAG TTG     354
Gly Glu Val Pro Asn Arg Gly Trp Arg His Trp Leu Glu Gly Glu Leu
                 75                  80                  85

CTG TAT CTG GAA CTG ACT GCA AGG GAT GCA GTG TGC GAG CAG GTC TTC     402
Leu Tyr Leu Glu Leu Thr Ala Arg Asp Ala Val Cys Glu Gln Val Phe
         90                  95                 100

AGG AAG GTC AGA TAGCCGGAGA GGAGCCAAGA TCCCTCCAGA CAGCACCAGC          454
Arg Lys Val Arg
        105

TCACAGACGC TCTTGTTGTG CCCCCTTCAA GCCCAGATTG TGCCAGGTCA GCTGTCCCTT     514

CCTCTGGCCA CCTTTCCTCC CTCTGGGTCC CTCCTCACCC CTCCCCGTGT TAATCTGTAA     574

CTTGGAGCCC CCAGGACAAA GTCCTTTCTC ACACTCCACT GCCCAATAGT GACCTCACTT     634

CCAGGTCAAG GTCTGGCGTC CCAAATGAAA GAAGCAGGCA AAGGGAAGGA GCCCTGAGG      694

ACAACCAATC TCCGCTCTCT CCTGTCCATT TGACCTCTTC TTTTCCTTCT AAGAAGAAC      754

TAAGCTTTGG GCATTGGCG ATTAGTGAAA ATTCTATCCT GATGGACTTC TGGAAAACTG      814

TGACTGGGGT TCAACAGTTT AAACAGGGGC TACTGGGGGA AAAAAAA                   861
```

(2) INFORMATION FOR SEQ ID NO:2:

(i) SEQUENCE CHARACTERISTICS:
        (A) LENGTH: 107 amino acids
        (B) TYPE: amino acid
        (D) TOPOLOGY: linear (ii) MOLECULE TYPE: protein (xi) SEQUENCE DESCRIPTION: SEQ ID NO:2:

```
Met Pro Pro Asn Leu Thr Gly Tyr Tyr Arg Phe Val Ser Gln Lys Asn
 1               5                  10                  15

Met Glu Asp Tyr Leu Gln Ala Leu Asn Ile Ser Leu Ala Val Arg Lys
             20                  25                  30

Ile Ala Leu Leu Leu Lys Pro Asp Lys Glu Ile Glu His Gln Gly Asn
         35                  40                  45

His Met Thr Val Arg Thr Leu Ser Thr Phe Arg Asn Tyr Thr Leu Gln
 50                  55                  60
```

```
Phe  Asp  Val  Gly  Val  Gln  Lys  Gly  Glu  Val  Pro  Asn  Arg  Gly  Trp  Arg
 65                        70                       75                         80

His  Trp  Leu  Glu  Gly  Glu  Leu  Leu  Tyr  Leu  Glu  Leu  Thr  Ala  Arg  Asp
                     85                       90                        95

Ala  Val  Cys  Glu  Gln  Val  Phe  Arg  Lys  Val  Arg
                100                      105
```

( 2 ) INFORMATION FOR SEQ ID NO:3:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

```
CGCGGATCCA  TGCCTCCCAA  CCTCACTG                                              28
```

( 2 ) INFORMATION FOR SEQ ID NO:4:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

```
GCGTCTAGAC  TATCTGACCT  TCCTGAAGAC                                            30
```

( 2 ) INFORMATION FOR SEQ ID NO:5:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

```
CGCGGATCCC  CCTCCCAACC  TCACTGGCTA  C                                         31
```

( 2 ) INFORMATION FOR SEQ ID NO:6:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

```
CGCGGATCCC  TATCTGACCT  TCCTGAAGA                                             29
```

( 2 ) INFORMATION FOR SEQ ID NO:7:

( i ) SEQUENCE CHARACTERISTICS:
        ( A ) LENGTH: 131 amino acids
        ( B ) TYPE: amino acid
        ( C ) STRANDEDNESS: single
        ( D ) TOPOLOGY: linear ( i i ) MOLECULE TYPE: protein (xi) SEQUENCE DESCRIPTION: SEQ ID NO:7:

```
Met Ala Asp Ala Phe Val Gly Thr Trp Lys Leu Val Asp Ser Lys Asn
 1               5                  10                 15
Phe Asp Asp Tyr Met Lys Ser Leu Gly Val Gly Phe Ala Thr Arg Gln
                20                  25                 30
Val Ala Ser Met Thr Lys Pro Thr Thr Ile Ile Glu Lys Asn Gly Asp
             35              40                 45
Thr Ile Thr Ile Lys Thr Gln Ser Thr Phe Lys Asn Thr Glu Ile Asn
     50                  55                 60
Phe Gln Leu Gly Ile Glu Phe Asp Glu Val Thr Ala Asp Asp Arg Lys
 65              70                 75                      80
Val Lys Ser Leu Val Thr Leu Asp Gly Gly Lys Leu Ile His Val Gln
                 85                 90                      95
Lys Trp Asn Gly Gln Glu Thr Thr Leu Thr Arg Glu Leu Val Asp Gly
            100                 105                110
Lys Leu Ile Leu Thr Leu Thr His Gly Ser Val Val Ser Thr Arg Thr
        115                 120                125
Tyr Glu Lys
    130
```

(2) INFORMATION FOR SEQ ID NO:8:

(i) SEQUENCE CHARACTERISTICS:
(A) LENGTH: 135 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:8:

```
Met Pro Val Asp Phe Asn Gly Tyr Trp Lys Met Leu Ser Asn Glu Asn
 1               5                  10                 15
Phe Glu Glu Tyr Leu Arg Ala Leu Asp Val Asn Val Ala Leu Arg Lys
                20                  25                 30
Ile Ala Asn Leu Leu Lys Pro Asp Lys Glu Ile Val Gln Asp Gly Asp
             35              40                 45
His Met Ile Ile Arg Thr Leu Ser Thr Phe Arg Asn Tyr Ile Met Asp
     50                  55                 60
Phe Gln Val Gly Lys Glu Phe Glu Glu Asp Leu Thr Gly Ile Asp Asp
 65              70                 75                      80
Arg Lys Cys Met Thr Thr Val Ser Trp Asp Gly Asp Lys Leu Gln Cys
             85                  90                      95
Val Gln Lys Gly Glu Lys Glu Gly Arg Gly Trp Thr Gln Trp Ile Glu
            100                 105                110
Gly Asp Glu Leu His Leu Glu Met Arg Ala Glu Gly Val Thr Cys Lys
        115                 120                 125
Gln Val Phe Lys Lys Val His
    130                 135
```

(2) INFORMATION FOR SEQ ID NO:9:

(i) SEQUENCE CHARACTERISTICS:
(A) LENGTH: 133 amino acids
(B) TYPE: amino acid
(C) STRANDEDNESS: single
(D) TOPOLOGY: linear (ii) MOLECULE TYPE: protein ( x i ) SEQUENCE DESCRIPTION: SEQ ID NO:9:

| Met | Thr | Arg | Asp | Gln | Asn | Gly | Thr | Trp | Glu | Met | Glu | Ser | Asn | Glu | Asn |
|---|---|---|---|---|---|---|---|---|---|---|---|---|---|---|---|
| 1 | | | | 5 | | | | | 10 | | | | | 15 | |
| Phe | Glu | Gly | Tyr | Met | Lys | Ala | Leu | Asp | Ile | Asp | Phe | Ala | Thr | Pro | Lys |
| | | | 20 | | | | | 25 | | | | | 30 | | |
| Ile | Ala | Val | Arg | Leu | Thr | Thr | Lys | Val | Ile | Asp | Gln | Asp | Gly | Asp | Asn |
| | | 35 | | | | | 40 | | | | | 45 | | | |
| Phe | Lys | Thr | Lys | Thr | Thr | Ser | Thr | Phe | Arg | Asn | Tyr | Asp | Val | Asp | Phe |
| | 50 | | | | | 55 | | | | | 60 | | | | |
| Thr | Val | Gly | Val | Glu | Phe | Asp | Glu | Tyr | Thr | Lys | Ser | Leu | Asp | Asn | Arg |
| 65 | | | | | 70 | | | | | 75 | | | | | 80 |
| His | Val | Lys | Ala | Leu | Val | Thr | Trp | Glu | Gly | Asp | Val | Leu | Val | Cys | Val |
| | | | | 85 | | | | | 90 | | | | | 95 | |
| Gln | Lys | Gly | Glu | Lys | Glu | Asn | Arg | Gly | Trp | Lys | Gln | Trp | Ile | Glu | Gly |
| | | | 100 | | | | | 105 | | | | | 110 | | |
| Asp | Lys | Leu | Tyr | Leu | Glu | Leu | Thr | Cys | Gly | Asp | Gln | Val | Cys | Arg | Gln |
| | | 115 | | | | | 120 | | | | | 125 | | | |
| Val | Phe | Lys | Lys | Lys | | | | | | | | | | | |
| | | 130 | | | | | | | | | | | | | |

( 2 ) INFORMATION FOR SEQ ID NO:10:

( i ) SEQUENCE CHARACTERISTICS:
        ( A ) LENGTH: 133 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:10:

| Met | Val | Asp | Ala | Phe | Leu | Gly | Thr | Trp | Lys | Leu | Val | Asp | Ser | Lys | Asn |
|---|---|---|---|---|---|---|---|---|---|---|---|---|---|---|---|
| 1 | | | | 5 | | | | | 10 | | | | | 15 | |
| Phe | Asp | Asp | Tyr | Met | Lys | Ser | Leu | Gly | Val | Gly | Phe | Ala | Thr | Arg | Gln |
| | | | 20 | | | | | 25 | | | | | 30 | | |
| Val | Ala | Ser | Met | Thr | Lys | Pro | Thr | Thr | Ile | Ile | Glu | Lys | Asn | Gly | Asp |
| | | 35 | | | | | 40 | | | | | 45 | | | |
| Ile | Leu | Thr | Leu | Lys | Thr | His | Ser | Thr | Phe | Lys | Asn | Thr | Glu | Ile | Ser |
| | 50 | | | | | 55 | | | | | 60 | | | | |
| Phe | Lys | Leu | Gly | Val | Glu | Phe | Asp | Glu | Thr | Thr | Ala | Asp | Asp | Arg | Lys |
| 65 | | | | | 70 | | | | | 75 | | | | | 80 |
| Val | Lys | Ser | Ile | Val | Thr | Leu | Asp | Gly | Gly | Lys | Leu | Val | His | Leu | Gln |
| | | | | 85 | | | | | 90 | | | | | 95 | |
| Lys | Trp | Asp | Gly | Gln | Glu | Thr | Thr | Leu | Val | Arg | Glu | Leu | Ile | Asp | Gly |
| | | | 100 | | | | | 105 | | | | | 110 | | |
| Lys | Leu | Ile | Leu | Thr | Leu | Thr | His | Gly | Thr | Ala | Val | Cys | Thr | Arg | Thr |
| | | 115 | | | | | 120 | | | | | 125 | | | |
| Tyr | Glu | Lys | Glu | Ala | | | | | | | | | | | |
| | | 130 | | | | | | | | | | | | | |

( 2 ) INFORMATION FOR SEQ ID NO:11:

( i ) SEQUENCE CHARACTERISTICS:
        ( A ) LENGTH: 132 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:11:

| Met<br>1 | Ser | Asn | Lys | Phe<br>5 | Leu | Gly | Thr | Trp | Lys<br>10 | Leu | Val | Ser | Ser | Glu<br>15 | Asn |
|---|---|---|---|---|---|---|---|---|---|---|---|---|---|---|---|
| Phe | Asp | Asp | Tyr<br>20 | Met | Lys | Ala | Leu | Gly<br>25 | Val | Gly | Leu | Ala | Thr<br>30 | Arg | Lys |
| Leu | Gly | Asn<br>35 | Leu | Ala | Lys | Pro | Thr<br>40 | Val | Ile | Ile | Ser | Lys<br>45 | Lys | Gly | Asp |
| Ile | Ile<br>50 | Thr | Ile | Arg | Thr | Glu<br>55 | Ser | Thr | Phe | Lys | Asn<br>60 | Thr | Glu | Ile | Ser |
| Phe<br>65 | Lys | Leu | Gly | Gln | Glu<br>70 | Phe | Glu | Glu | Thr | Thr<br>75 | Ala | Asp | Asn | Arg | Lys<br>80 |
| Thr | Lys | Ser | Ile | Val<br>85 | Thr | Leu | Gln | Arg | Gly<br>90 | Ser | Leu | Asn | Gln | Val<br>95 | Gln |
| Arg | Trp | Asp | Gly<br>100 | Lys | Glu | Thr | Thr | Ile<br>105 | Lys | Arg | Lys | Leu | Val<br>110 | Asn | Gly |
| Lys | Met | Val<br>115 | Ala | Glu | Cys | Lys | Met<br>120 | Lys | Gly | Val | Val | Cys<br>125 | Thr | Arg | Ile |
| Tyr | Glu<br>130 | Lys | Val | | | | | | | | | | | | |

What is claimed is:

1. An isolated nucleic acid molecule comprising a polynucleotide selected from the group consisting of:
   (a) a polynucleotide encoding the cytostatin I polypeptide having the deduced amino acid sequence of FIG. 1 (SEQ ID NO 2);
   (b) a polynucleotide encoding the cytostatin I polypeptide having the amino acid sequence encoded by the cDNA Contained in ATCC Deposit No. 97103; and
   (c) a polynucleotide having a nucleotide sequence at least 95% identical to the nucleotide sequence of the cDNA contained in ATCC Deposit No. 97103 which encodes cytostatin I.

2. The isolated nucleic acid molecule of claim 1 wherein the polynucleotide is DNA.

3. The isolated nucleic acid molecule of claim 1 wherein the polynucleotide is RNA.

4. The isolated nucleic acid molecule of claim 2 wherein said polynucleotide encodes cytostatin I having the deduced amino acid sequence of FIG. 1 (SEQ ID NO 2).

5. The isolated nucleic acid molecule of claim 2 wherein said polynucleotide encodes the cytostatin I polypeptide encoded by the cDNA of ATCC Deposit No. 97103.

6. The isolated nucleic acid molecule of claim 1 which encodes mature cytostatin I as shown in FIG. 1 (SEQ ID NO 1).

7. The isolated nucleic acid molecule of claim 2 which encodes mature cytostatin I deposited as ATCC Deposit No. 97103.

8. A vector containing the DNA of claim 2.

9. A host cell containing the vector of claim 8.

10. A process for producing a cytostatin I polypeptide comprising: expressing from the host cell of claim 9 the polypeptide encoded by said DNA and recovering said expressed protein.

11. A process for producing cells capable of expressing a cytostatin I polypeptide comprising transfecting cells with the vector of claim 8.

12. The isolated nucleic acid molecule of claim 1, wherein said polynucleotide is 95% identical to the nucleotide sequence of the cDNA contained in ATCC Deposit No. 97103 which encodes mature cytostatin I.

* * * * *

UNITED STATES PATENT AND TRADEMARK OFFICE
CERTIFICATE OF CORRECTION

PATENT NO : 5,658,758
DATED : August 19, 1997
INVENTOR(S) : Jian NI; Reiner GENTZ; Guo-Liang YU; and Craig A. ROSEN It is certified that error appears in the above-identified patent and that said Letters Patent is hereby corrected as shown below:

Title page, before item [57], add Attorney Agent or Firm --Robert H. Benson --.

Title page, insert item [73], Assignee name, after item [76], Inventors:

-- Human Genome Sciences, Inc., Rockville, Maryland --.

Signed and Sealed this

Twenty-second Day of December, 1998

*Attest:*

BRUCE LEHMAN

*Attesting Officer*  *Commissioner of Patents and Trademarks*